(12) United States Patent
Thaning et al.

(10) Patent No.: US 9,827,334 B2
(45) Date of Patent: Nov. 28, 2017

(54) PREPARATION OF IOFORMINOL, AN X-RAY CONTRAST AGENT

(71) Applicant: GE Healthcare AS, Oslo (NO)

(72) Inventors: Mikkel Thaning, Oslo (NO); Andreas Olsson, Oslo (NO); Christian Glogard, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 14/430,148

(22) PCT Filed: Sep. 17, 2013

(86) PCT No.: PCT/US2013/060092
§ 371 (c)(1),
(2) Date: Mar. 20, 2015

(87) PCT Pub. No.: WO2014/052092
PCT Pub. Date: Apr. 3, 2014

(65) Prior Publication Data
US 2015/0265727 A1   Sep. 24, 2015

(30) Foreign Application Priority Data

Sep. 27, 2012 (NO) ................................ 20121103

(51) Int. Cl.
*A61K 49/00* (2006.01)
*A61K 49/04* (2006.01)
*C07C 231/12* (2006.01)
*C07C 237/46* (2006.01)

(52) U.S. Cl.
CPC ........ *A61K 49/0438* (2013.01); *C07C 231/12* (2013.01); *C07C 237/46* (2013.01)

(58) Field of Classification Search
CPC ...... A61K 49/00; C07C 231/12; C07C 237/46
See application file for complete search history.

(56) References Cited

U.S. PATENT DOCUMENTS

| 5,698,739 | A | 12/1997 | Sovak |
| 8,920,780 | B2 | 12/2014 | Thaning |
| 2008/0267884 | A1 | 10/2008 | Axelsson et al. |
| 2010/0322868 | A1* | 12/2010 | Thaning ............. A61K 49/0433 424/9.452 |
| 2013/0116554 | A1 | 5/2013 | Kaiser et al. |

FOREIGN PATENT DOCUMENTS

| CN | 102816085 A | 12/2012 |
| EP | 0406992 B1 | 3/1995 |
| EP | 2593143 A1 | 5/2013 |
| EP | 2178568 B1 | 7/2014 |
| EP | 2900631 A1 | 8/2015 |
| JP | 3249112 B2 | 1/2002 |
| JP | 2010533172 A | 10/2010 |
| JP | 2013-531685 A | 8/2013 |
| JP | 2016193921 A | 11/2016 |
| RU | 2385316 C2 | 3/2010 |
| WO | 2006/016815 A1 | 2/2006 |
| WO | 2007055580 A1 | 5/2007 |
| WO | 2009008734 A2 | 1/2009 |
| WO | WO2009008734 * | 1/2009 |
| WO | 2012007456 A1 | 1/2012 |
| WO | 2014/052092 A1 | 4/2014 |

OTHER PUBLICATIONS

International Search Report and Written Opinion from corresponding PCT application No. PCT/US2013/060092 dated Dec. 3, 2013; 10 pages.
Japan Notice of Preliminary Rejection for Japanese Patent Application No. 2015534550, dated Jul. 18, 2017, 8 pages.
International Preliminary Report on Patentability for PCT Patent Application PCT/US2013/060092, dated Apr. 9, 2015, 8 pages.
Office Action Received for Corresponding Russian Patent Application 2015107017/04, dated Jul. 25, 2017, 11 pages (5 pages of English Transition + 6 Pages of official Copy.

* cited by examiner

*Primary Examiner* — Michael G Hartley
*Assistant Examiner* — Jagadishwar Samala
(74) *Attorney, Agent, or Firm* — Wood IP LLC

(57) ABSTRACT

The present invention relates to a process for the preparation of Ioforminol, a contrast agent useful in X-ray imaging. More particularly, the invention relates to preparation of Ioforminol from a compound mixture comprising 1-formylamino-3,5-bis(2,3-bis(formyloxy)propan-1-ylcarbamoyl)-2,4,6-trioodobenzene by a process comprising in situ hydrolysis and a bis-alkylation.

19 Claims, No Drawings

PREPARATION OF IOFORMINOL, AN X-RAY CONTRAST AGENT

This application is a filing under 35 U.S.C. 371 of international application number PCT/US2013/060092, filed Sep. 17, 2013, which claims priority to Norway application number 20121103, filed Sep. 27, 2012, the entire disclosure of each of which is hereby incorporated by reference.

The present invention relates to a process for the preparation of iodinated X-ray contrast agents and in particular to a process for preparing Ioforminol, a contrast agent useful in X-ray imaging. More particularly, the invention relates to preparation of Ioforminol from a compound mixture comprising 1-formylamino-3,5-bis(2,3-bis(formyloxy)propan-1-ylcarbamoyl)-2,4,6-trioodobenzene, a key intermediate in the process for preparing Ioforminol.

For the last 50 years the field of X-ray contrast agents has been dominated by soluble iodine containing compounds. Commercial available contrast media containing iodinated contrast agents are usually classified as ionic monomers such as diatrizoate (Gastrografen™), ionic dimers such as ioxaglate (Hexabrix™) nonionic monomers such as iohexol (Omnipaque™), iopamidol (Isovue™), iomeprol (Iomeron™) and the non-ionic dimer iodixanol (Visipaque™). The most widely used commercial non-ionic X-ray contrast agents such as those mentioned above are considered safe. Contrast media containing iodinated contrast agents are used in more than 20 million of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The part of the patient population considered as high risk patients is increasing. To meet the need for continuous improvement of in vivo X-ray diagnostic agents for the entire patient population, there is a continuous drive in finding X-ray contrast agents that have improved properties, also with regards to contrast induced nephrotoxicity (CIN).

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Currently, one contrast medium having an iodinated non-ionic dimer as the active pharmaceutical ingredient is on the market, the product Visipaque™ containing the compound iodixanol.

In WO2009/008734 of the applicant a novel dimeric contrast agent named Ioforminol is disclosed. The properties of this is described in more detail in the publications Chai et al. "Predicting cardiotoxicity propensity of the novel iodinated contrast medium GE-145: ventricular fibrillation during left coronary arteriography in pigs", Acta Radiol, 2010, and in Wistrand, L. G., et al "GE-145, a new low-osmolar dimeric radiographic contrast medium", Acta Radiol, 2010. Ioforminol (GE-145) is named Compound 1 herein and has the following structure:

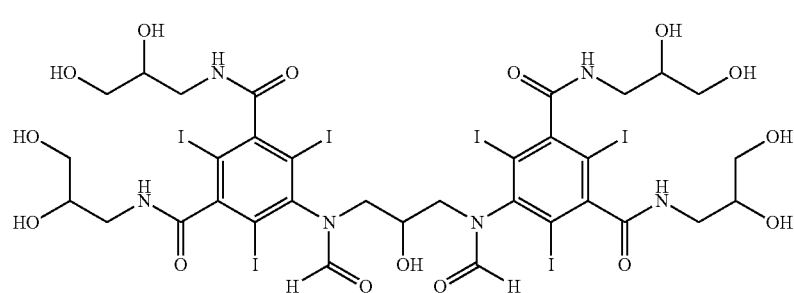

Compound 1

5,5'-(2-Hydroxypropane-1,3-diyl)bis(formylazanediyl)bis($N^1,N^3$-bis(2,3-dihydroxypropyl)-2,4,6-triiodoisophthalamide)

The manufacture of non-ionic X-ray contrast media involves the production of the chemical drug, the active pharmaceutical ingredient (API), i.e. the contrast agent, followed by the formulation into the drug product, herein denoted the X-ray composition. WO2009/008734 of the applicant provides a synthetic route for preparing the API Ioforminol. Ioforminol can e.g., as provided by the general preparation description and Example 1 of WO2009/008734, be synthesized from 5-amino-N,N'-bis-(2,3-dihydroxy-propyl)-2,4,6-triiodo-isophthalamide (compound (4)), which is commercially available. The preparation of this compound is known from the synthesis of both iohexol and iodixanol and can also be prepared from 5-nitroisophthalic acid for instance as described in WO2006/016815, including hydrogenation and subsequent iodination e.g. by iodine chloride, ICI. Alternatively, 5-amino-2,4,6-triiodoisophthalic acid may be used, which is commercially available precursor, e.g. from Sigma-Aldrich. The free amino group of the isophthalamide compound (compound (4)) is then acylated and the hydroxyl groups in the substituents may also be protected by acylation. The protecting groups may be removed for example by hydrolysis to give $N^1,N^3$-bis(2,3-dihydroxypropyl)-5-formylamino-2,4,6-triiodoisophthalamide. In a dimerization step this is reacted e.g. in a bisalkylation of epichlorohydrin to provide the Ioforminol contrast agent compound.

The state of the art synthesis of Ioforminol, as disclosed in examples 1 and 2 of WO2009/008734, is shown in Scheme 1 below.

Scheme 1.

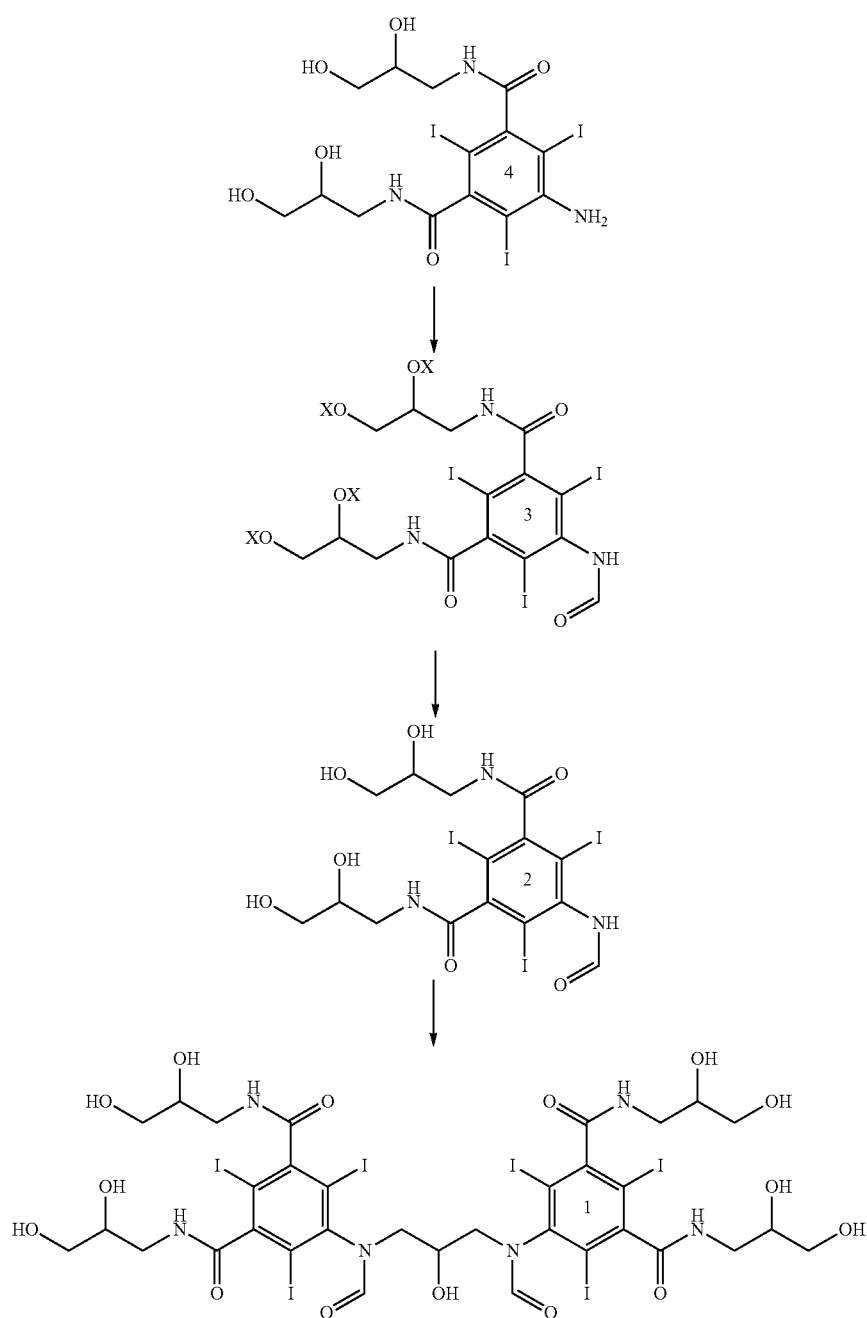

As described in WO2009/008734 compound 3 is a mixture comprising 1-formylamino-3,5-bis(2,3-bis(formyloxy)propan-1-ylcarbamoyl)-2,4,6-triiodobenzene, and X is then a formyl group.

In each synthetic step it is important to optimize the yield, minimize the production of impurities, but also to minimize time and costs spent. The problem to be solved by the present invention may be regarded as the provision of optimizing the process for preparation of Ioforminol from the compound (3) of scheme 1, i.e. a mixture comprising 1-formylamino-3,5-bis(2,3-bis(formyloxy)propan-1-ylcarbamoyl)-2,4,6-triiodobenzene. The invention is hence directed to a process comprising a hydrolysis of compound (3) and a dimerization reaction to provide Ioforminol.

In the state of the art process, as disclosed in WO2009/008734, Example 2, procedure B, preparation of Compound (1) (Ioforminol) from 1-formylamino-3,5-bis(2,3-bis(formyloxy)propan-1-ylcarbamoyl)-2,4,6-triiodobenzene (compound (3) wherein X is a formyl-group) is performed in a process wherein compound (3) was solved in a mixture of water and methanol, further comprising boric acid, at a pH of 11.6-11.7 by addition of potassium hydroxide. When in solution epichlorohydrin was added in several portions. The mixture was left stirring and the pH was adjusted several times by addition of potassium hydroxide at the same time as the temperature was regulated. The whole process for preparation of Compound (1) from Compound (3) was reported to be at least 48 hours.

A more cost efficient process has been sought for preparation of Ioforminol (compound (1)) wherein reaction time is reduced and wherein the yield of Compound (1) is increased. We have now found that preparation of Compound (1) can be done in a cost-efficient and environmentally friendly process involving in situ hydrolysis of the protecting groups of compound (3), followed by a bis-alkylation, also denoted a dimerization, by using water as the only solvent. A process taking considerably shorter time than the state of art process has been identified.

Accordingly, in a first aspect the invention provides a process for preparation of Compound (1)

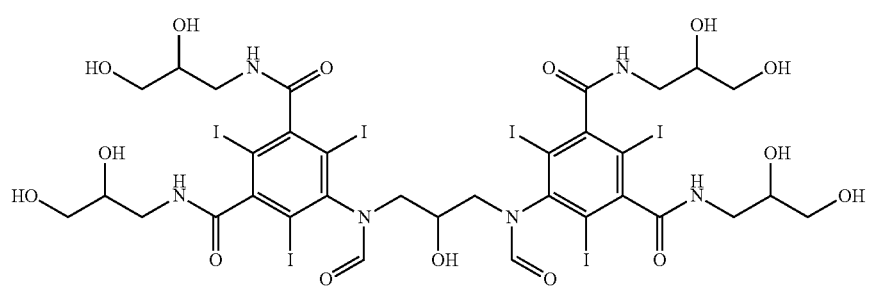

Compound (1)

from compound (3)

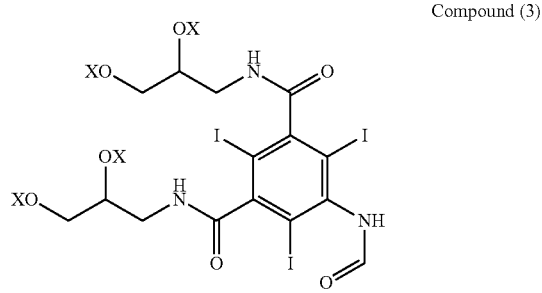

Compound (3)

wherein each X individually denotes hydrogen, a formyl group (—CO—H) or an acetyl group (—CO—CH₃);
the process comprising a step of in situ hydrolysis of the protecting groups (—OX) of compound (3), wherein compound (3) is suspended in water only.

Compound (3) is a mixture of different compounds with both formyl and acetyl protecting groups. This comes as a result of the earlier formylating step wherein compound (3) is prepared from compound (4) preferably using mixed anhydrides. In one embodiment compound 3 comprises a mixture of compounds wherein all X groups are individually formyl or acetyl. The main component of compound (3) is 1-formylamino-3,5-bis(2,3-bis(formyloxy)propan-1-ylcarbamoyl)-2,4,6-triodobenzene. Hence, in one embodiment all X groups denote formyl.

In one embodiment of the invention the process comprises the sequential steps of
 i) suspending compound (3) in water;
 ii) adjusting the pH of the solution of step i) to 10.0-12.5; before a bis-alkylation reaction.

When compound (3) has been suspended, and the pH has been adjusted, an in situ hydrolysis of the formyl and acetyl protecting groups of compound (3) takes place. In this reaction, compound (2) is prepared, but this is not isolated. At the same time formyl- and acetyl salts are generated as biproducts. This generation of salts may have the effect of accelerating the rate of the bis-alkylation reaction taking place after the in situ hydrolysis, providing a rapid and complete bis-alkylation. An unexpected increase in reaction rate has been seen for the bis-alkylation when suspending the starting material compound (3) in water only and using this in situ hydrolysis procedure. The generated salts are believed to increase the reaction rate by coordinating the dialkylating agent used in the bis-alkylation and/or stabilising the transition state of the reaction. At the same time the process provides a high yield. It has been found that the reaction from compound (3) to compound (1) can be performed in less than 24 hours, such as less than 20 hours, and providing a yield of 90% or higher, such as 93% or up to or above 95%. Surprisingly, the water-only-step of the process of the invention provides about 20% higher yield and saves about one day in production time, compared to the prior art process as described in Example 2 of WO2009/008734.

In step i) water is used as the single solvent, and no addition of other solvents or additives, such as e.g. boric acid, has surprisingly been found needed. In the process of the invention the starting material compound (3) is preferably a fine powder with low acid content. The mixture of compound (3) may in one embodiment comprise some rests of antisolvents, such as alcohols, but no alcohol is needed to be added. In a process of making compound (3) a short chain alcohol may be used to optimize the preparation of this in powder form, and it has been found beneficial that the compound (3) as used as the starting material in the currently claimed process is not dried completely, but comprises 0-15% alcohol, and a rest alcohol content of 0-7%, and most preferably 2-5%, is appropriate. The rest alcohol in compound (3) is typically a short chain alcohol being a C1-C6 straight or branched alcohol, or a mixture of such. The alcohol may be monohydroxylated or dihydroxylated. Methanol, ethanol and propanols are preferred alcohols, with propanols, particularly iso-propanol, being most preferred. The amount of water needed for optimal reaction conditions depends on factors like the content of rest alcohol and the temperature. An appropriate amount of water has been found to be about 0.5-2.0 liter water/kg compound (3), such as about 1 liter water/kg compound (3).

In step ii, hence before the bis-alkylation reaction) the pH is adjusted to 10.0-12.5, and more preferably to 11.0-1.8, and most preferably to 11.0-11.2, by the addition of a base to the compound (3) suspension. The pH adjustment is preferably done stepwise to neutralise acids and to avoid too sudden heat generation. The base is selected from strong water-soluble bases such as sodium hydroxide and potassium hydroxide wherein a sodium hydroxide solution (e.g. 50%) is preferred. The addition of the base provides a base-driven hydrolysis of the protecting ester groups of compound (3), wherein formyl- and acetyl salts, such as sodium formyl- and sodium acetyl salts, are generated as bi products. In addition this pH adjustment provides the optimal pH conditions for the bis-alkylation. In one embodiment, the pH adjustment is performed using a pH-stat system to ensure that the pH is kept stationary. Such pH system includes both an acid and a base, for instance HCl and NaOH solutions.

The bis-alkylation (dimerization step) via a 2-hydroxypropane bridge preferably takes place by addition of an appropriate amount of a dialkylating agent to the basic solution of step (ii). Such agent is selected from dihalo-substituted alkanol or halo-substituted heterocycloalkyl, such as 1,3-dichloro-2-propanol, 1-chloro-2,3-propanol, 1,3-dibromo-2-hydroxypropane and epichlorohydrin (EPI), wherein EPI is particularly preferred. Accordingly, in a further embodiment of the invention the process further comprises the step of adding a dialkylating agent to the basic solution of step ii). The dialkylating agent is added to the basic aqueous solution in one or more portions, such as in 1 to 5 portions, preferably 3 equal portions. About 2 molar equivalents of compound (3) is reacted and bridged with one molar equivalent of the dialkylating agent. A slight molar excess of the dialkylating agent may be used due to a slight consumption of the dialkylating agent by the base. During and after the addition the reaction mixture is kept under stirring for a period needed to run the bis-alkylation reaction to completion. This may take 5-20 hours, preferably 10-15 hours.

Before, during and/or after the hydrolysis, the temperature may also be adjusted, such as being cooled below room temperature, e.g. to 12-16° C. or lower. In a preferred embodiment, the temperature is adjusted to about 15° C. before addition of the dialkylating agent. Particularly preferred, the pH is adjusted to 11.0-11.2 and the temperature is adjusted to about 15° C. before the addition, and these conditions are kept to the bis-alkylation has run to completion.

The compounds prepared, such as compound (1), may be purified in any convenient manner, e.g. by washing, by preparative chromatography, by recrystallization or ultra/nano-filtration. Optional additional steps are hence purification and drying.

Compound mixture (3) and compound (1) as prepared by the claimed process comprise optical active isomers and will exist in several isomeric forms due to chiral carbon atoms. In addition, the compounds exhibit exo/endo isomerism due to the restricted rotation of the N—CO bond in the formyl function caused by the proximity of the bulk iodine atom. Both preparation of enantiomerically pure products as well as mixtures of optical isomers are encompassed by the process of the invention.

The compounds prepared according to the invention may be used as contrast agents and may be formulated with conventional carriers and excipients to produce diagnostic contrast media. Thus viewed from further aspects the invention provides Ioforminol (compound (1)), and a diagnostic composition comprising Ioforminol, prepared according to the process of the invention, wherein the composition comprises at least one physiologically tolerable carrier or excipient, e.g. an aqueous solution for injection optionally together with added plasma ions or dissolved oxygen. The contrast agent composition of the invention may be in a ready to use concentration or may be a concentrate form for dilution prior to administration. Hence, the invention further embraces use of Ioforminol prepared according to the process of preparation, and a diagnostic composition containing such, in X-ray contrast examinations.

The invention is illustrated with reference to the following non-limiting examples.

EXAMPLES

Example 1

Preparation of Compound (1) from Compound (3)

Compound (3) (1103 kg, 890 mol) was suspended in water (1213 L) using a reactor with overhead mechanical stirring. The suspension was cooled to 10 degrees and aqueous NaOH (50%) was added for 12 h keeping the pH and temperature below 12.5 and 20 degrees, respectively. The solution was cooled to 16 degrees and the pH was set to 11.1 using a pH stat system charged with HCl (30%) and NaOH (50%). The system was left running as long as the temperature was <18 degrees. EPI (41 kg, 445 mol) was added continuously over a period of 2.5 h keeping the temperature between 15-18 degrees. After stirring for 38 h the reaction mixture was quenched by adjusting the pH to 7 using HCl (30%). HPLC showed ~95.5% UV yield of compound (1).

The dialkylation reaction time was prolonged in this example to ensure completion and maximize the yield. The reaction can be quenched considerably earlier, such as 10-12 hours, without significant loss of yield.

The invention claimed is:
1. A process for preparation of Compound (1)

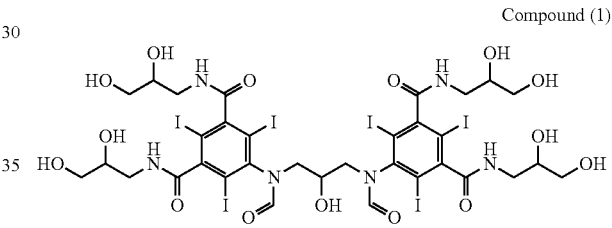

Compound (1)

from a composition comprising compound (3) in situ,

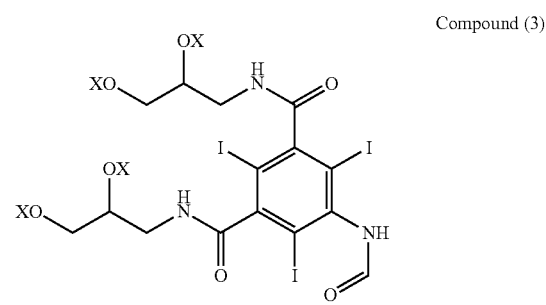

Compound (3)

wherein each X of compound (3) individually denotes hydrogen, a formyl group (—CO—H) or an acetyl group (—CO—CH3) and the composition of compound (3) comprises 0-15% $C_1$-$C_6$ straight or branched alcohol that is mono- or di- hydroxylated;

said process comprising, suspending the composition of compound (3) in water such that the amount of water is about 0.25-2.0 litre water/kg compound (3), adjusting and maintaining the pH and temperature of the suspension between 10.0 -12.5 and below room temperature, respectively to allow compound (3) to hydrolyze to compound (2) in water without additives or organic solvent(s), and

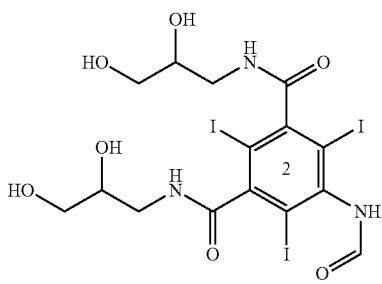 [SMILES: O=CNc1c(I)c(C(=O)NCC(O)CO)c(I)c(C(=O)NCC(O)CO)c1I]

adding a dialkylating agent to carry out bis-alkylation of compound (2) to form compound (1) in situ,
wherein the process is performed in less than 24 hours and provides a conversion of compound (3) to compound (1) with a yield of 90% or higher.

2. The process of claim 1, wherein the $C_1$-$C_6$ straight or branched alcohol is methanol, ethanol, propanol, or iso-propanol.

3. The process of claim 1 wherein the composition comprising compound (3) is a fine powder with low acid content.

4. The process of claim 1 wherein the composition of compound (3) comprises 2-5% alcohol.

5. The process of claim 1, wherein the dialkylating agent is a dihalo-substituted alkanol or halo-substituted heterocycloalkyl.

6. The process of claim 5 wherein the dialkylating agent is epichlorohydrin.

7. The process of claim 1, wherein the temperature of the hydrolysis step is maintained between 12-16° C.

8. The process of claim 1, wherein the pH of the hydrolysis step is adjusted by a strong water soluble base and the base is selected from sodium hydroxide and potassium hydroxide.

9. The process of claim 1, wherein the dialkylation agent is selected from 1,3-dichloro-2-propanol, 1-chloro-2,3-propanol, and 1,3-dibromo-2-hydroxypropane.

10. A process for preparation of Compound (1)

Compound (1)

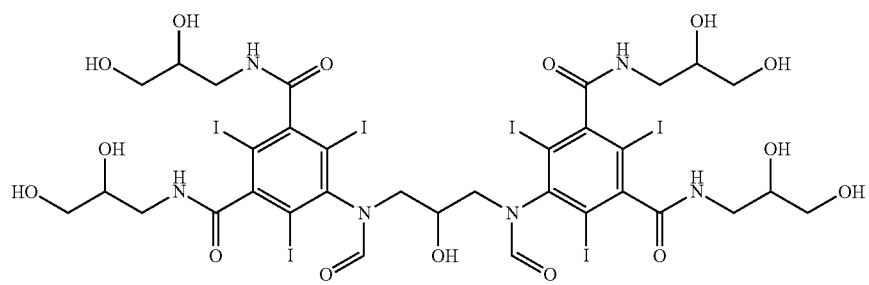

from a composition comprising compound (3) in situ,

Compound (3)

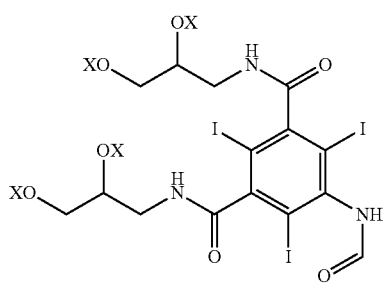 [SMILES: O=CNc1c(I)c(C(=O)NCC(O)CO)c(I)c(C(=O)NCC(O)CO)c1I]

wherein each X of compound (3) individually denotes hydrogen, a formyl group (—CO—H) or an acetyl group (—CO—CH$_3$) and the composition of compound (3) comprises 2-5% alcohol;
said process comprising,
suspending the composition of compound (3) in water such that the amount of water is about 0.25 -2.0 litre water/kg compound (3),
adjusting and maintaining the pH and temperature of the suspension between 10.0-12.5 and 12-16° C., respectively using a strong water soluble base to allow compound (3) to hydrolyze to compound (2), and

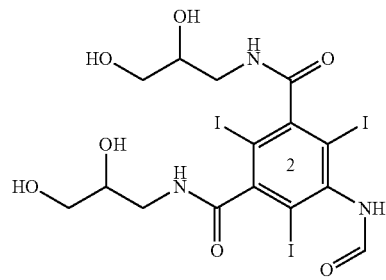

adding a dialkylating agent to carry out bis-alkylation of compound (2) to form compound (1) in situ,
wherein the alcohol is methanol, ethanol, propanol, or iso-propanol,
wherein the dialkylation agent is selected from 1,3-dichloro-2-propanol, 1-chloro-2,3-propanol, 1,3-dibromo-2-hydroxypropane, and epichlorohydrin, and
wherein the process is performed in less than 24 hours and provides a conversion of compound (3) to compound (1) with a yield of 90% or higher.

11. The process of claim 10, wherein the strong water soluble base is sodium hydroxide, potassium hydroxide, or aqueous solution thereof.

12. The process of claim 10, wherein the alcohol is iso-propanol.

13. The process of claim 10, wherein the dialkylation agent is epichlorohydrin.

14. The process of claim 10, wherein the strong water soluble base is aqueous sodium hydroxide.

15. The process of claim 10, wherein the process is carried out in water without additives or organic solvents.

16. The process of claim 10, wherein the process provides a conversion of compound (3) to compound (1) with a yield of 93% or higher.

17. A process for preparation of Compound (1)

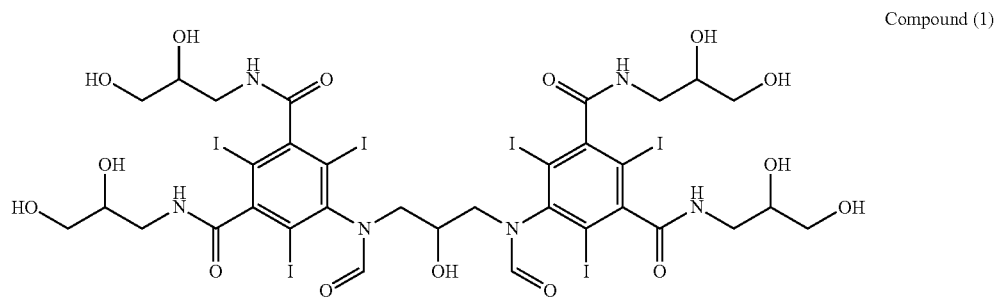 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound (1)

from a composition comprising compound (3) in situ,

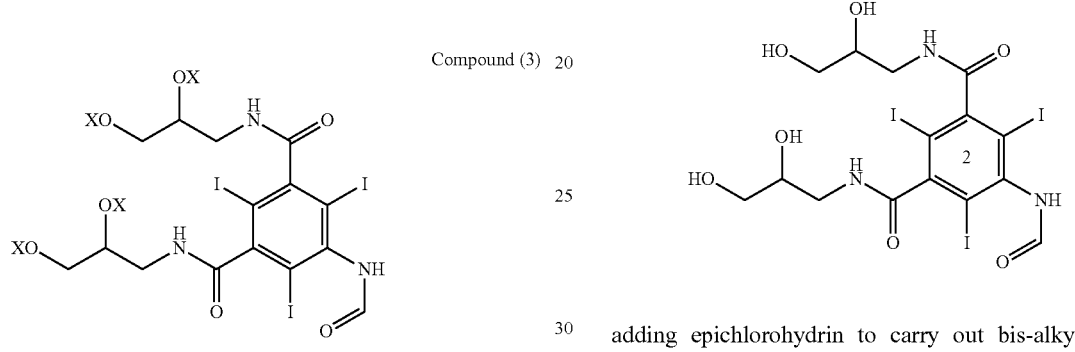

Compound (3)

wherein each X of compound (3) individually denotes hydrogen, a formyl group (—CO—H) or an acetyl group (—CO—CH$_3$) and the composition of compound (3) comprises 2-5% alcohol;
said process comprising,
suspending the composition of compound (3) in water such that the amount of water is about 0.25 -2.0 litre water/kg compound (3),
adjusting and maintaining the pH and temperature of the suspension between 10.0 -12.5 and 12-16 ° C., respectively using aqueous sodium hydroxide to allow compound (3) to hydrolyze to compound (2), and adding epichlorohydrin to carry out bis-alkylation of compound (2) to form compound (1) in situ,
wherein the alcohol iso-propanol, and
wherein the process is performed in less than 24 hours and provides a conversion of compound (3) to compound (1) with a yield of 90% or higher.

18. The process of claim 17, wherein the process is carried out in water without additives or organic solvents.

19. The process of claim 17, wherein the process provides a conversion of compound (3) to compound (1) with a yield of 93% or higher.

* * * * *